United States Patent [19]
Yoshikami

[11] Patent Number: 5,252,492
[45] Date of Patent: Oct. 12, 1993

[54] FLUORESCENCE ASSAY FOR LIGAND OR RECEPTOR UTILIZING SIZE EXCLUSION

[75] Inventor: Doju Yoshikami, Salt Lake City, Utah

[73] Assignee: University of Utah Research Foundation, Salt Lake City, Utah

[21] Appl. No.: 668,237

[22] Filed: Mar. 12, 1991

[51] Int. Cl.$^5$ .................. G01N 33/50; G01N 33/53
[52] U.S. Cl. .................... 436/501; 436/536; 436/537; 436/538; 436/514; 436/517; 436/800; 436/805; 436/807; 436/810; 435/4; 435/7.1; 435/7.8; 435/7.9; 435/803; 435/808; 435/968; 435/971
[58] Field of Search ............... 436/501, 514, 515, 535, 436/537, 538, 541, 172

[56] References Cited

U.S. PATENT DOCUMENTS

| | | | |
|---|---|---|---|
| 3,442,819 | 5/1969 | Herbert | 436/541 |
| 4,205,952 | 6/1980 | Cais | 436/518 |
| 4,350,760 | 9/1982 | Nicolas et al. | 436/515 |
| 4,410,660 | 10/1983 | Straus | 436/811 |
| 4,459,361 | 7/1984 | Gefter | 436/541 |
| 4,645,747 | 2/1987 | Cais et al. | 436/500 |
| 4,895,809 | 1/1990 | Schlabach et al. | 436/514 |
| 5,045,479 | 9/1991 | Newman et al. | 436/172 |

OTHER PUBLICATIONS

Elkins, Roger et al. "Fluorescence spectroscopy and its application to a new generation of high sensitivity, multi-microspot, multianalyte, immunoassay", Clinica Chimica Acta, 194 (1990) pp. 91-114, May.

Gosling, James P. "A decade of development in immunoassay methodology", Clin. Chem. 36/8 (1990) pp. 1408-1427, Aug.

*Primary Examiner*—Christine M. Nucker
*Assistant Examiner*—Chris Dubrule
*Attorney, Agent, or Firm*—Terry M. Crellin

[57] ABSTRACT

A method disclosed for studying the interaction in solution of two molecules of the type such as a ligand and a receptor that are capable of reacting or binding with each other. The method comprises preparing an aliquot of a solution containing the first of the molecules. The second of the molecules is then added to the aliquot. A fluorescently labeled molecule is added to the aliquot, wherein the fluorescently labeled molecule is also capable of reacting or binding with the second of the molecules. A porous matrix that is optically transparent is immersed into the aliquot containing the two molecules being studied and the fluorescently labeled molecule, wherein the second molecule and any fluorescently labeled molecule bound thereto is sterically hindered from permeating the porous, optically transparent matrix, while any unbound fluorescently labeled molecule permeates the matrix. The matrix that has been immersed into the aliquot is then viewed with means such as a fluorescent microscope for determining the amount of fluorescence emitted from the matrix.

11 Claims, 1 Drawing Sheet

FLUORESCENCE ASSAY FOR LIGAND OR RECEPTOR UTILIZING SIZE EXCLUSION

GOVERNMENT SUPPORT

This invention was made with Government support under Grant 5R01 GM38919-03 awarded by the National Institutes of Health. The Government has certain rights in the invention.

BACKGROUND OF THE INVENTION

1. Field of the Invention

The present invention relates to a novel, simple and accurate method for studying interaction of a native ligand and its receptor using a fluorescently labeled, indicator ligand and a porous, optically transparent matrix that can be permeated by the fluorescently labeled ligand but is partially or totally impermeable to the labeled ligand when it is bound to the receptor. Fluorescence emitted from within the porous matrix is then useful as an indicator of the interaction between the native ligand and the receptor.

State 2. of the Art

Interaction of a ligand and a receptor in solution has been assayed or studied in the past by complicated techniques using differently labeled components. One such method is to use a radioactively labeled ligand or receptor. Another method is to utilize a fluorescent dye that is attached to the ligand or receptor. Generally, however, it has been necessary to isolate the reactants or products by complicated procedures. For example, special procedures have been necessary to separate bound from unbound ligands.

In U.S. Pat. No. 4,816,419 a method for fluorescence ligand binding assays is disclosed wherein certain surfactants that form micelles in solution were found to be useful in effecting differential fluorescence between bound and unbound ligands. The micelles sequester bound from unbound labeled ligands. Capture of labeled ligands occurs preferentially for free labeled ligands. When the labeled ligands are bound to a receptor, capture by the micelles is severely inhibited. The fluorescent emission is different when the labeled ligands are captured by the micelles than when the bound labeled ligands are not captured.

The method using the micelles of U.S. Pat. No. 4,816,419 is severely restricted in the breadth of ligands and receptors that can be analyzed or studied. The method employing the micelles is chemical in nature, thereby being restricted to the study of ligands and receptors bound to the ligands that interact in specific ways with the micelles. The ligands must be bound to or combine with the micelles, and the ligands bound to the receptor must not be attracted to or combine with the micelles.

3. Objectives

A principal objective of the invention is to provide a novel, simple, accurate, fast, economical method of studying and assaying the interaction of two molecules, such as a ligand and its receptor, in solution utilizing the measurement of fluorescence within an optically transparent matrix that is differentially permeable to the molecules depending upon the size of the molecules.

A particular objective of the present invention is to provide such a method of studying the interaction of two molecules in solution wherein a fluorescently labeled molecule is used that can permeate a porous, optically transparent matrix, with the reaction product of the labeled molecule and the other molecule being partially or totally excluded from the matrix, wherein the matrix is then viewed, such as through a fluorescent microscope, to determine fluorescence emitted from within the matrix.

Another objective of the present invention is to provide such a method of studying the interaction of two molecules in solution that does not rely upon chemical dependency of either of the molecules with the means being used to differentiate between the molecules, but rather utilizes the physical size of the molecules such that one of the molecules permeates a porous, optically transparent matrix but the other molecule is partially or totally excluded from the matrix.

BRIEF DESCRIPTION OF THE INVENTION

The above objectives are achieved in accordance with the present invention by providing novel, unique method of studying and quantitatively assaying the interaction of two molecules, such as a ligand and its receptor, in solution. The method involves the measurement of fluorescence within an optically transparent matrix which is differentially permeable to molecules depending on their sizes. Different matrixes may be used, such as dextran gels, polyacrylamide gels, cellulose membranes, porous glass or other porous, inert materials that can be substantially readily permeated by the one molecule but which hamper and inhibit permeation thereof by the other molecule. The fluorescence within the matrix is measured with various devices, including a conventional optical fluorescent microscope.

The reagents in the study or assay are the receptor, the native ligand and a functional, fluorescently labeled, ligand (either the native ligand derivatized with a fluorescent reporter moiety, or a fluorescent analog of the native ligand). A matrix is selected which sterically excludes the receptor or the receptor-fluorescent ligand complex, but does not exclude the fluorescent ligand itself. When the matrix is immersed in a solution containing the fluorescent ligand alone, the fluorescent ligand will permeate the matrix and render the matrix fluorescent. However, when receptor is also in the solution, the fluorescence emitted by the matrix will be reduced because the fluorescent ligand bound to the receptor is totally or in part excluded from the matrix. On the other hand, if native ligand is also in the solution, it would preoccupy the receptor. Consequently, fewer fluorescent ligand molecules would be bound to receptor and therefor be excluded from the matrix. Thus, the presence of native ligand would be manifested by increased emission of fluorescence from the matrix.

The novel method of the invention can be used to study the interactions of a variety of different kinds of molecules. For example, the interactions of antigen with antibody; nucleic acid with nucleic acid or protein; drug, hormone, neurotoxin or neurotransmitter with receptor; and substrate with enzyme can be studied. The method of the invention can be used as a qualitative and quantitative assay for these molecules. In addition, the method of the invention may be used to characterize the kinetics and binding constants of the interactions of these molecules. The assay may also be used to estimate the molecular weights of functional receptors. The assay may also be used to continuously monitor the effluent of a chromatographic column, or the blood or interstitial fluid of a patient, for specific molecules. The method of the present invention has advantageous utility in clinical, industrial, and educational settings as well as in basic research.

The method of the present invention has many advantages over methods of the prior art. The method of the present invention is simple both in concept and execution. It circumvents the need for special manipulations to separate bound from unbound ligand which is a serious drawback of most prior art procedures. The assay is rapid, with measurements being performed in seconds, and under optimal conditions, binding of ligand with receptor can be monitored in real time. The assay is frugal in that the matrix material may be reused and very little reagent material is required. The assay volumes can be sub-nanoliter, requiring sub-femtomole amounts of ligand and receptor.

Additional objects and features of the invention will become apparent from the following detailed description, taken together with the accompanying drawing.

THE DRAWING

The drawing shows a graph of emitted fluorescence from a matrix used in an example which is set out hereinafter.

DETAILED DESCRIPTION OF PREFERRED EMBODIMENTS

Figure 1:
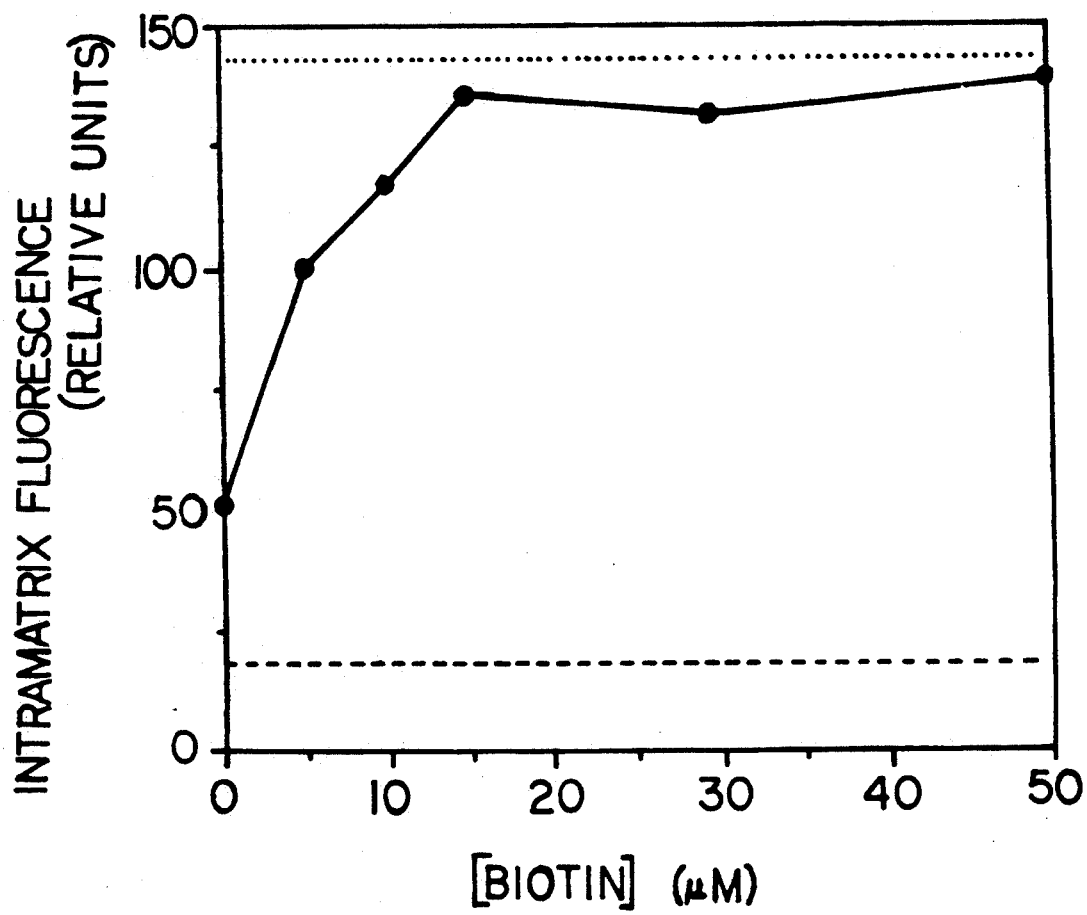

In accordance with the present invention, an improved method is provided for studying and assaying the interaction of two molecules in solution. Generally, the two molecules are a ligand and its receptor, but numerous other interactive molecules can be studied and assayed. In the discussions that follow, the two molecules will be referred to as ligand and receptor, but that is not intended as a limitation of the scope of the invention as claimed in the claims appended hereto.

The method comprises first preparing an aliquot of a solution containing one of the molecules being studied or assayed. As mentioned, this molecule generally will be a ligand and will be referred to as such hereinafter. The other of the two molecules, which will generally be a receptor for the ligand and will be referred to hereinafter as a receptor, is added to the aliquot. The second molecule, i.e., the receptor, is of course capable of binding or reacting with the first molecule, i.e., the ligand. A fluorescently labeled molecule, such as a fluorescently labeled ligand, is then added to the aliquot containing the other two molecules. The fluorescently labeled molecule must be capable of binding or reacting with the second molecule, i.e., the receptor of the two molecules being studied or assayed.

A porous matrix that is optically transparent is immersed into the aliquot containing the two molecules and the fluorescently labeled molecule. The matrix is a substantially inert material that has pores or openings therein. The pores or openings in the matrix will generally be of microscopic size and smaller than the size of the larger of the molecules being studied or assayed. The pores or openings of the matrix can be readily permeated only by molecules having sizes no larger than the pores or openings in the matrix. Thus, the larger of the molecules being studied or assayed is sterically hindered from permeating the matrix. The smaller of the molecules being studied or assayed will have a size that will allow the molecules to permeate the matrix. Of course, any smaller molecules, including the fluorescently labeled molecules, that are bound or reacted with the larger molecules will be sterically hindered from permeating the matrix.

The matrix that has been immersed into the aliquot is then viewed with means for determining the amount of fluorescence emitted from the matrix. The amount of fluorescence will, of course, be indicative of the interaction of the two molecules that are being studied or assayed.

As mentioned above, the first molecule, the smaller of the molecules, is preferably a native ligand, and the second molecule, the larger of the molecules, is preferably a receptor of the native ligand. The fluorescently labeled molecule is preferably a fluorescently labeled ligand that is capable of binding with the receptor, with the labeled ligand having a size small enough that unbound labeled ligand is able to permeate the matrix. The means for viewing the matrix to observe fluorescence emitting therefrom is preferably a fluorescence microscope.

Although the method of the present invention can be advantageously performed using distinct, separate aliquots of the solution to be analyzed, with the other reagents being added to that aliquot, the method can also be used to analyze continuously a flow of solution. In this latter mode, the method can be advantageously used to continuously monitor such streams as the effluent of a chromatographic column or the blood or interstitial fluid of a patient for specific molecules. The aliquots being tested become successive portions of the solution as it flows in a channel from an upstream position past the porous matrix that is positioned in the channel. The reagents, including the other of the two molecules and the fluorescently labeled molecules are added to the solution as the solution flows through the channel upstream of the porous matrix. The aliquots thus form a continuous stream flowing through the channel and past the porous matrix, with the other reagents being continuously added to the stream flowing through the channel upstream of the porous matrix.

The method of the present invention is ideally suitable for assaying the interaction of a ligand and its receptor in solution. A plurality of samples of standard solutions are prepared in which each sample contains a known concentration of a native ligand. Each sample further has a concentration of native ligand that varies from the other samples. A predetermined amount of a receptor is added to an aliquot of each of the samples. The receptor is, of course, capable of binding with the native ligand. A predetermined amount of a fluorescently labeled ligand is added to each aliquot. The receptor is further, of course, capable of binding with the fluorescently labeled ligand.

A porous matrix that is optically transparent is immersed into each aliquots containing the native ligand, the added fluorescently labeled ligand and the added receptor. The receptor and any ligands bound thereto in each of the aliquots is sterically hindered from permeating the porous, optionally transparent matrix, while any unbound labeled ligand permeates the matrix. The matrix from each aliquot is viewed with a means for determining the amount of fluorescence emitted from the matrix.

An aliquot of a test solution containing an unknown concentration of native ligand is then treated by adding thereto the same predetermined amount of receptor as used in each of the aliquots of the samples of the standard solutions. The same predetermined amount of fluorescently labeled ligand as used in each of the aliquots of the samples of the standard solutions is then added to the aliquot of the test solution.

A matrix which is the same as those used with the standard solutions is immersed into the aliquot of the test solution, and the matrix is viewed with a means for determine the amount of fluorescence emitted from the matrix. The concentration of the native ligand in the test solution can then be determined by comparing the amount of fluorescence emitted from the matrix employed with the test solution and the fluorescence emitted from the matrixes employed with the standard solutions.

The method of the present invention can just as well be used for assaying the receptor in solution. The method is similar to that previously described. First, a plurality of samples of standard solutions are prepared in which each sample contains a known concentration of a receptor, but each sample has a concentration of receptor that varies from the other samples. A predetermined amount of a fluorescently labeled ligand is added to each aliquot, with the receptor being capable of binding with the fluorescently labeled ligand.

A porous matrix that is optically transparent is immersed into each of the aliquots containing the receptor and the added fluorescently labeled ligand. The receptor and any ligand bound thereto in each of the aliquots is sterically hindered from permeating the porous, optically transparent matrix, while any unbound labeled ligand permeates the matrix. The matrix from each aliquot is viewed with a means for determining the amount of fluorescence emitted from the matrix.

An aliquot of a test solution containing an unknown concentration of receptor is then treated by adding thereto the same predetermined amount of fluorescently labeled ligand as used in each aliquot of the samples of the standard solution. A matrix which is the same as those used with the standard solutions is immersed into the aliquot of the test solution, and the matrix is viewed with a means for determine the amount of fluorescence emitted from the matrix. The concentration of the receptor in the test solution can be determined by comparing the amount of fluorescence emitted from the matrix employed with the test solution and the fluorescence emitted from the matrixes employed with the standard solutions.

The method of the present invention can be modified to achieve an assay for a ligand, wherein the procedure is much similar to standard titration type procedures. The procedure comprises the following steps:

(a) An aliquot of a solution containing an unknown concentration of a native ligand is prepared.

(b) A predetermined amount of a receptor is added to the aliquot, wherein the receptor is capable of binding with the native ligand.

(c) A predetermined amount of a fluorescently labeled ligand is added to the aliquot, wherein the fluorescently labeled ligand is capable of binding with the receptor.

(d) A porous matrix that is optically transparent is immersed into the aliquot containing the native ligand, the added fluorescently labeled ligand and the added receptor. The receptor and any ligands bound thereto are sterically hindered from permeating the porous, optically transparent matrix, while any unbound labeled ligand permeates the matrix.

(e) The matrix is viewed with a means for determining the amount of fluorescence emitted from the matrix.

(f) Steps (a) through (e) are repeated to determine amounts of the labeled ligand and receptor added to the aliquot at which a particular amount of fluorescence is emitted from the matrix.

(g) The concentration of the native ligand in the solution is determined from the known amounts of labeled ligand and receptor at which a particular amount of fluorescence is emitted from the matrix.

The immediately preceding method can further be adapted to assay for the receptor. When assaying for the receptor, the steps of the procedure comprise:

(a) An aliquot of a solution containing an unknown concentration of a receptor is prepared.

(b) A predetermined amount of a fluorescently labeled ligand is added to the aliquot, wherein the fluorescently labeled ligand is capable of binding with the receptor.

(c) A porous matrix that is optically transparent is immersed into the aliquot containing the receptor and the added fluorescently labeled ligand. The receptor arid any ligand bound thereto in the aliquot is sterically hindered from permeating the porous, optically transparent matrix, while any unbound labeled ligand permeates the matrix.

(d) The matrix is viewed with a means for determining the amount of fluorescence emitted from the matrix;

(e) Steps (a) through (d) are repeated to determine amounts of the ligand and labeled ligand added to the aliquot at which a particular fluorescence is emitted from the matrix.

(f) The concentration of the receptor in the solution is determined from the known amounts of labeled ligand at which a particular amount of fluorescence is emitted from the matrix.

The method of the present invention can further be modified to resemble a continuous titration procedure. When assaying for a ligand the continuous procedure comprises the steps:

(a) A predetermined amount of a receptor is added to an aliquot Of a solution Containing an unknown concentration of a native ligand. The receptor is capable of binding with the native ligand.

(b) A porous matrix that is optically transparent is immersed into the aliquot containing the native ligand and the added receptor, wherein the receptor and any ligands bound thereto in the aliquot are sterically hindered from permeating the porous, optically transparent matrix.

(c) A fluorescently labeled ligand that is capable of binding with the receptor is added to the aliquot, wherein the resulting fluorescently labeled ligand bound to the receptor is hindered from permeating the matrix, but any excess unbound fluorescently labeled ligand in the aliquot can permeate the matrix. The fluorescently labeled ligand is added in an amount just sufficient so that the matrix emits a particular amount of fluorescence when the matrix is viewed with a means for determining amounts of fluorescence emitted from the matrix.

(d) The concentration of the native ligand in the solution is determined from the known amounts of labeled ligand and receptor at which a particular amount of fluorescence is emitted from the matrix.

The immediately preceding method can further be adapted to assay the receptor. When assaying for the receptor, the steps of the procedure comprise:

(a) A porous matrix that is optically transparent is immersed into an aliquot of a solution containing an unknown concentration of a receptor;

(b) A fluorescently labeled ligand that is capable of binding with the receptor is added to the aliquot. Any fluorescently labeled ligand bound to the receptor is hindered from permeating the matrix, but any excess unbound fluorescently labeled ligand in the aliquot can permeate the matrix. The fluorescently labeled ligand is added in an amount just sufficient so that the matrix emits a particular amount of fluorescence when the matrix is viewed with a means for determining amounts of fluorescence emitted from the matrix.

(c) The concentration of the receptor in the solution is determined from the known amounts of fluorescently labeled ligand at which a particular amount of fluorescence is emitted from the matrix.

The method of the present invention will now be illustrated by the following example. A system was used in which the ligand was biotin and the receptor was avidin. The fluorescently labeled ligand was a fluorescent derivative of biotin synthesized by first coupling cysteine to biotin via an amino group. The cysteine adduct was then reacted with Lucifer yellow VS to yield the fluorescently labeled "biotin-yellow." The binding of biotin to avidin is essentially irreversible. Further, there is a large difference in size between biotin-yellow (molecular weight approximately 1000) and avidin kmolecular weight approximately 68,000).

All test solutions contained physiological saline consisting of tin (in mM) NaCl (111), $CaCl_2$ (1.8), LCL (2), NaHEPES, pH 7.2 (10) supplemented with 1 mg/ml vovine serum albumin, 0.2 mg/ml lysozyme and 0.02% $NaN_3$. The proteins were present to minimize non-specific binding, and azide was present as a bactericide.

The steric exclusion matrix was cross-linked dextran in bead form which was obtained commercially. The dextran beads are normally used as medium for gel filtration chromatography. The dextran beads employed in this example are conventionally used to chromatography fractionate peptides and globular proteins in the molecular weight range of 1,500 to 30,000. Thus, avidin is largely excluded from the dextran when used as the matrix, and biotin-yellow is readily able to permeate such matrix.

Sample solutions containing a fixed concentration of avidin were exposed to various concentrations of biotin for one minute. Following this, a fixed amount of biotin-yellow was added to the solution, and the matrix (approximately 100 beads of the dextran) was added to the solution.

Each sample was transferred to a hemacytometer, coverslipped, placed on a microscope stage and viewed with a fluorescence microscope. The microscope was focused on one of the beads of the matrix, and the fluorescence emitted by the bead was measured.

Each data point on the curve of FIG. 1 represents the average fluorescence intensity of six beads in each sample. As can be seen, the fluorescence increases as the concentration of biotin in the mixture is increased. This clearly indicates that as the biotin binding sites on avidin were increasingly preoccupied by biotin, corresponding fewer molecules of biotin-yellow were excluded from the matrix. The dashed line represents the fluorescence when no biotin-yellow was present in the solutions, and the dotted line represents the fluorescence when avidin was absent from the solutions.

As will be recognized, the curve of FIG. 1 becomes a calibration standard that can be used in assaying other solutions containing the Ligand biotin. For example, if a solution containing an unknown amount of biotin were treated in accordance with the above example, and the fluorescence emitted by the matrix for the test solution was 120 on the scale for fluorescence, the amount of biotin in the test sample could be read as 10 $\mu$M from FIG. 1.

It should now be appreciated that the method of the present invention will work regardless of the sizes of fluorescent ligand and receptor, provided a steric exclusion matrix is used whose pores or openings have sizes that discriminate between the fluorescent ligand alone and when it is bound to the receptor. Furthermore, the matrix need not totally exclude the fluorescent ligand-receptor complex. The method of the present invention is useful whenever the complex is sufficiently less permeant than the fluorescent ligand alone so that a fluorometrically detectable difference can be detected.

The rate of diffusion of the fluorescent ligand between extra- and intramatrix space can be maximized by use Of thin matrixes. When the rate of diffusion of the fluorescent ligand between extra- and intramatrix space is rapid with respect to the rate of association or dissociation of ligand with receptor, then the kinetics of ligand-receptor interactions may be determined by use of an immobilized steric exclusion matrix whose intramatrix fluorescence is continuously monitored by a device with adequate time resolution. Below are presented examples of how kinetic constants of association and dissociation can be experimentally determined.

Consider the simplest bimolecular case where the interaction of fluorescent ligand (F-L) with receptor (R) forms the fluorescent ligand-receptor complex (F-L:R).

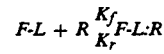

$$F\text{-}L + R \underset{K_r}{\overset{K_f}{\rightleftharpoons}} F\text{-}L\text{:}R$$

The forward (or association) rate constant is given by $k_f$, and the reverse (or dissociation) rate constant is $k_r$. These rates can be determined using the method of the present invention. For determining the forward rate constant $k_f$, the matrix is first equilibrated with F-L. At time t, an excess of receptor is introduced into the solution in which the matrix is bathed. The free [F-L], and likewise intramatrix fluorescence, will decrease with time. The rate of association of F-L with R should obey pseudo first-order kinetics. Thus, the ln of intramatrix fluorescence as a function of time will be a straight line with a slope equal to $<k_f[R]$.

For determining the reverse rate constant $k_r$, the matrix is first equilibrated with a solution containing F-L and R (and necessarily therefore, F-L:R). At time t=0, a high concentration of native ligand is introduced into the solution so as to occlude the ligand-binding sites on R, and thereby association of F-L with R is prevented, although dissociation of F-L from R is not. The free [F-L], and likewise intramatrix fluorescence, will increase with time. The rate of dissociation of F-L from R should obey first-order kinetics. Thus, the ln of the relative amount of F-L:R remaining, i.e., 1-$\{f(t)-f(0)\}/\{f(\infty)-f(0)\}$, where f(t) is the intramatrix fluorescence at time t, should be a straight line with a slope that is equal to $-K_r$.

The method of the present invention can also be used to determine the molecular weight of the fluorescent ligand-receptor complex. The exclusion of fluorescent ligand-receptor complex from matrixes with known exclusion characteristics may be used to deduce the approximate molecular weights of the complex, just as conventional gel filtration chromatography does. The advantage of the present method is in its simplicity.

Further, the method of the present invention can be used to assay the activity of any agent whose activity results in an alteration in size of a fluorescent adduct. For example, the activity of hydrolytic enzymes such as proteases can be measured by use of fluorescently labeled substrates that are susceptible to enzymatic cleavage. Residues in a protein may be labeled with fluorescent groups. Exposure of the protein to a degradative enzyme will clip the protein into smaller fragments. The present method can be used to measure the activity of the enzyme by use of a matrix which excludes the intact protein, but not its fragments.

Although preferred embodiments of the method of the present invention have been illustrated and described, it is to be understood that the present disclosure is made by way example and that various other embodiments are possible without departing from the subject matter coming within the scope of the following claims, which subject matter is regarded as the invention.

I claim:

1. A method for studying the interaction of two molecules in solution, said method comprises
   (a) preparing an aliquot of a solution containing one of the molecules;
   (b) adding the other of the two molecules to said aliquot, wherein the other molecule is capable of binding with said one molecule;
   (c) adding a fluorescently labeled molecule to said aliquot, wherein the fluorescently labeled molecule is capable of binding with said other molecule;
   (d) immersing a porous matrix that is initially transparent into said aliquot containing the two molecules and the fluorescently labeled molecule, said matrix consisting of a material that (i) has pores or openings therein which are of a microscopic size that is smaller than the size of said other of the molecules, and (ii) is substantially inert and does not react chemically or immunlogically with any of the molecules being studies, wherein said other molecule and any fluorescently labeled molecule bound thereto in said aliquot are sterically hindered from permeating the porous, optically transparent matrix, while any unbound fluorescently labeled molecule permeates the matrix; and
   (e) viewing the matrix while the matrix is in fluid contact with said aliquot with means for determining the amount of fluorescence emitted from the matrix.

2. A method in accordance with claim 1, wherein said one molecule is a native ligand, said other molecule is a receptor of the native ligand, and the fluorescently labeled molecule is a fluorescently labeled ligand that is capable of binding with the receptor.

3. A method in accordance with claim 1, wherein the means for viewing the matrix in step (e) is a fluorescence microscope.

4. A method for assaying the interaction of a ligand and its receptor is solution, said method comprises
   for preparing a plurality of samples of standard solutions in which each sample contains a known concentration of a native ligand, but each sample has a concentration of native ligand that varies from the other samples;
   (b) adding a predetermined amount of a receptor to an aliquot of each of said samples, wherein the receptor is capable of binding with said native ligand;
   (c) adding a predetermined amount of a fluorescently labeled ligand to each said aliquot, wherein the receptor is capable of binding with the fluorescently labeled ligand;
   (d) immersing a porous matrix that is optically transparent into each said aliquot containing the native ligand, the added fluorescently labeled ligand and the added receptor, said matrix consisting of a material that (i) has pores or openings therein which are of a microscopic size that is smaller than the size of the receptor, and (ii) is substantially inert and does not react chemically or immunologically with the ligand or receptor, wherein the receptor and any ligands bound thereto in each said aliquot are sterically hindered from permeating the porous, optically transparent matrix, while any unbound labeled ligand permeates the matrix;
   (e) viewing the matrix while the matrix is in contact with that aliquot with a means for determining the amount of fluorescence emitted from the matrix;
   (f) adding the same predetermined amount of receptor as used in step (b) to an aliquot of a test solution containing an unknown concentration of native ligand;
   (g) adding the same predetermined amount of fluorescently labeled ligand as used in step (c) to the aliquot of solution from step (f),
   (h) immersing a matrix which is made of the same material as those used in step (d) into the aliquot of solution from step (g);
   (i) viewing the matrix from step (h) while the matrix is in fluid contact with said aliquot of solution from step (g) with a means for determine the amount of fluorescence emitted from the matrix; and
   (j) determining the concentration of native ligand in the solution from which the aliquot of step (f) was taken by comparing the amount of fluorescence emitted from the matrix of each of the aliquots in steps (e) and (i).

5. A method in accordance with claim 4, wherein the means for viewing the matrixes in steps (e) and (i) is a fluorescence microscope.

6. A method for assaying the interaction of a ligand and its receptor in solution, said method comprises
   (a) preparing a plurality of samples of standard solutions in which each sample contains a known concentration of a receptor, but each sample has a concentration of receptor that varies from the other samples;
   (b) adding a predetermined amount of a fluorescently labeled ligand to an aliquot of each of said samples, wherein the receptor is capable of binding with the fluorescently labeled ligand;
   (c) immersing a porous matrix that is optically transparent into each said aliquot containing the receptor and the added fluorescently labeled ligand, said matrix consisting of a material that (i) has pores or openings therein which are of a microscopic size that is smaller than the size of the receptor, and (ii) is substantially inert and does not react chemically or immunologically with the ligand or receptor, wherein the receptor and any ligand bound thereto in each said aliquot is sterically hindered from permeating the porous, optically transparent matrix, while any unbound labeled ligand permeates the matrix;

(d) viewing the matrix while the matrix is in contact with each said aliquot with a means for determining the amount of fluorescence emitted from the matrix;

(e) adding the same predetermined amount of fluorescently labeled ligand as used in step (b) to an aliquot of a test solution containing an unknown concentration of receptor;

(f) immersing a matrix which is made of the same material as those used in step (c) into the aliquot of solution from step (e);

(g) viewing the matrix from step (f) while that matrix is in contact with said aliquot of solution from step (e) with a means for determine the amount of fluorescence emitted from the matrix; and (h) determining the concentration of the receptor in the solution from which the aliquot of step (e) was taken by comparing the amount of fluorescence emitted from the matrix of each of the aliquots in steps (d) and (g).

7. A method in accordance with claim 6, wherein the means for viewing the matrixes in steps (d) and (g) is a fluorescence microscope.

8. A method for assaying the interaction of a ligand and its receptor in solution, said method comprises (a) adding a predetermined amount of a receptor to an aliquot of a solution containing an unknown concentration of a native ligand, wherein the receptor is capable of binding with said native ligand;

(b) immersing a porous matrix that is optically transparent into said aliquot containing the native ligand and the added receptor, said matrix consisting of a material that (i) has pores or openings therein which are of a microscopic size that is smaller than the size of the receptor, and (ii) is substantially inert and does not react chemically or immunlogically with the ligand or receptor, wherein the receptor and any ligands bound thereto in said aliquot are sterically hindered from permeating the porous, optically transparent matrix;

(c) adding a fluorescently labeled ligand that is capable of binding with the receptor to said aliquot, wherein the resulting fluorescently labeled ligand bound to the receptor is hindered from permeating the matrix, but any excess unbound fluorescently labeled ligand in the aliquot can permeate the matrix, said fluorescently labeled ligand being added in an amount just sufficient so that the matrix emits a particular amount of fluorescence when the matrix is viewed while in contact with said aliquot with a means for determining amounts of fluorescence emitted from the matrix; and (d) determining the concentration of the native ligand in said solution from the known amounts of labeled ligand and receptor at which a particular amount of fluorescence is emitted from the matrix.

9. A method in accordance with claim 8, wherein the means for viewing the matrix in step (c) is a fluorescence microscope.

10. A method for assaying the interaction of a ligand and its receptor in solution, said method comprises (a) immersing a porous matrix that is optically transparent into an aliquot of a solution containing an unknown concentration of a receptor, said matrix consisting of a material that (i) has pores or openings therein which are of a microscopic size that is smaller than the size of the receptor, and (ii) is substantially inert and does not react chemically or immunlogically with the ligand or receptor;

(b) adding a fluorescently labeled ligand that is capable of binding with the receptor to said aliquot, wherein the resulting fluorescently labeled ligand bound to the receptor is hindered from permeating the matrix, but any excess unbound fluorescently labeled ligand in the aliquot can permeate the matrix, said fluorescently labeled ligand being added in an amount just sufficient so that the matrix emits a particular amount of fluorescence when the matrix is viewed while in contact with said aliquot with a means for determining amounts of fluorescence emitted from the matrix; and (c) determining the concentration of the receptor in said solution from the known amounts of fluorescently labeled ligand at which a particular amount of fluorescence is emitted from the matrix.

11. A method in accordance with claim 20, wherein the means for viewing the matrix in step (b) is a fluorescence microscope.

* * * * *